United States Patent
Fadakar

(10) Patent No.: US 7,482,495 B2
(45) Date of Patent: Jan. 27, 2009

(54) PROCESS FOR MAKING ALKYLENE GLYCOL ETHER COMPOSITIONS USEFUL FOR METAL RECOVERY

(75) Inventor: Farhad Fadakar, Downingtown, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 252 days.

(21) Appl. No.: 11/316,147

(22) Filed: Dec. 22, 2005

(65) Prior Publication Data

US 2007/0149825 A1    Jun. 28, 2007

(51) Int. Cl.
*C07C 43/11*    (2006.01)

(52) U.S. Cl. .................. 568/679; 568/618; 423/26; 209/166

(58) Field of Classification Search .................. None
See application file for complete search history.

(56) References Cited

U.S. PATENT DOCUMENTS

| | | | | |
|---|---|---|---|---|
| 2,611,485 A | 9/1952 | Tveter | .................. | 209/166 |
| 2,695,101 A | 11/1954 | Booth et al. | .................. | 209/166 |
| 3,595,390 A | 7/1971 | Booth | .................. | 209/166 |
| 3,829,505 A | 8/1974 | Herold | .................. | 260/611 B |
| 3,865,718 A * | 2/1975 | Tveter et al. | .................. | 209/166 |
| 4,269,702 A | 5/1981 | Milner et al. | .................. | 209/166 |
| 4,474,619 A | 10/1984 | Meyer et al. | .................. | 209/166 |
| 4,582,596 A | 4/1986 | Hansen et al. | .................. | 209/166 |
| 4,732,669 A * | 3/1988 | Nimerick | .................. | 209/166 |
| 4,929,344 A | 5/1990 | Fleming | .................. | 209/166 |
| 5,158,922 A | 10/1992 | Hinney et al. | .................. | 502/175 |
| 5,232,581 A | 8/1993 | Roberts et al. | .................. | 209/166 |
| 5,470,813 A | 11/1995 | Le-Khac | .................. | 502/175 |
| 5,482,908 A | 1/1996 | Le-Khac | .................. | 502/156 |

OTHER PUBLICATIONS

DOW, MSDS, Dec. 17, 2001, 7 pages.*
DOW, Chemistry of DOW Glycol Ether Products, (The Dow Chemical Company) 1995-2008, [online], [retrieved on Apr. 15, 2008]. Retrieved from The Dow Chemical Company using Internet <URL: http://www.dow.com/oxysolvents/lit/tech.htm.*
De Ketttenis P., Elsevier, *Toxicology Letters 156*, (Mar. 2005) 5-11.

* cited by examiner

*Primary Examiner*—Rosalynd Keys
(74) *Attorney, Agent, or Firm*—Jonathan L. Schuchardt

(57) ABSTRACT

A process for making an alkylene glycol ether composition is disclosed. In one aspect, the process comprises reacting propylene glycol methyl ether (PM) with from 1.5 to 3 equivalents of propylene oxide (PO). The resulting alkoxylation mixture is distilled to provide a composition comprising at least 30 wt. % of TPM and less than 20 wt. % of DPM. In another process of the invention, DPM reacts with from 0.5 to 1.5 equivalents of PO in similar fashion to make an analogous product. Also disclosed are alkylene glycol ether compositions made by the process of the invention and use of the compositions in a method for recovering metals from metallic ores by froth flotation.

8 Claims, No Drawings

PROCESS FOR MAKING ALKYLENE GLYCOL ETHER COMPOSITIONS USEFUL FOR METAL RECOVERY

FIELD OF THE INVENTION

The invention relates to a process for making alkylene glycol ether compositions useful for mining applications.

BACKGROUND OF THE INVENTION

Froth flotation is commonly used in the mining industry to recover mineral values from aqueous ore slurries. A wide variety of suitable frothing agents have been identified, although the best frother for a particular application is usually selected through experience or by trial and error. Alkyl or aryl ethers of propylene glycol and polypropylene is glycols have long been generally known as effective frothing agents for copper recovery (see, e.g., U.S. Pat. Nos. 2,611,485, 2,695,101, and 3,595,390).

The South African mining industry uses tripropylene glycol methyl ether (TPM) as a frothing agent for recovering platinum and other precious metals. While the product performs well, it is produced commercially as a by-product of the normal process for making propylene glycol methyl ether (PM) from methanol and propylene oxide. Consequently, TPM is expensive and in relatively short supply. Unfortunately, demand for TPM is still not sufficient to justify its "on purpose" manufacture.

The mining industry, particularly the platinum mining industry, would benefit from the availability of inexpensive alternatives to TPM that provide acceptable performance as frothing agents. Not all alkylene glycol ether compositions are suitable for use in platinum recovery. For example, our own evaluation of ethoxylated PM demonstrated unacceptable frothing performance.

SUMMARY OF THE INVENTION

The invention is a process for making an alkylene glycol ether composition. In one aspect, the process comprises reacting propylene glycol methyl ether (PM) with from 1.5 to 3 equivalents of propylene oxide (PO) in the presence of an alkoxylation catalyst. The resulting alkoxylation mixture comprises PM, dipropylene glycol methyl ethers (DPM), tripropylene glycol methyl ethers (TPM), and higher PM propoxylates. This alkoxylation mixture is then distilled to remove PM and DPM and provide a composition comprising at least 30 wt. % of TPM and less than 20 wt. % of DPM.

In another process of the invention, DPM reacts with from 0.5 to 1.5 equivalents of PO in similar fashion. The alkoxylation mixture, which comprises DPM, TPM, and higher DPM propoxylates, is then distilled to provide a composition comprising at least 30 wt. % TPM and less than 20 wt. % of DPM.

The invention includes alkylene glycol ether compositions made by the process of the invention and their use in a method for recovering metals from metallic ores by froth flotation.

DETAILED DESCRIPTION OF THE INVENTION

The invention is a process for making alkylene glycol ether compositions that are valuable for mining applications, particularly metal recovery by froth flotation.

In one process of the invention, propylene glycol methyl ether (PM) is reacted with from 1.5 to 3 equivalents of propylene oxide in the presence of an alkoxylation catalyst.

PM is usually prepared by the base-catalyzed reaction of methanol and propylene oxide (PO), followed by distillation. There are two PM isomers, known as "PM-1" (1-methoxy-2-propanol) and "PM-2" (2-methoxy-1-propanol). PM-1, the major product from methanol propoxylation, is the isomer sold commercially. PM-1 is available from Lyondell Chemical Company as ARCOSOLV® PM. For practicing the process of the invention, either or both PM isomers can be used, and "PM" refers herein to either or both PM-1 and PM-2.

When PM is the starter for the alkoxylation reaction, it is reacted with from 1.5 to 3 equivalents of propylene oxide. Preferably, propylene oxide is used in an amount within the range of 1.8 to 2.5 equivalents. Most preferred is the range from 1.9 to 2.1 equivalents.

An alkoxylation catalyst is used. The type of catalyst used is not critical. Suitable catalysts include alkali metals, alkali metal hydroxides, alkali metal alkoxides, and the like. Potassium hydroxide and sodium hydroxide are particularly preferred. Suitable catalysts also include double metal cyanide catalysts of the type described, for example, in U.S. Pat. Nos. 3,829,505, 5,158,922, 5,470,813, and 5,482,908, the teachings of which are incorporated herein by reference.

The reaction of PM and PO produces an alkoxylation mixture comprising unreacted PM, dipropylene glycol methyl ethers (DPM), tripropylene glycol methyl ethers (TPM), and higher PM propoxylates. This reaction mixture normally contains too much DPM to be valuable for froth flotation. Consequently, the alkoxylation mixture is distilled by any suitable technique, including vacuum stripping, to remove PM and DPM and provide an alkylene glycol ether composition comprising at least 30 wt. % of TPM and less than 20 wt. % of DPM. We found that such a mixture provides acceptable results in a laboratory-scale froth test used to approximate good performance in the field for recovering platinum values by froth flotation. The alkylene glycol ether composition preferably comprises less than 15 wt. % of DPM. Most preferably, the amount of DPM is within the range of 4 to 12 wt. %.

In another process of the invention, dipropylene glycol methyl ether (DPM) reacts with from 0.5 to 1.5 equivalents of propylene oxide in the presence of an alkoxylation catalyst to produce an alkoxylation mixture comprising DPM, TPM, and higher DPM propoxylates.

DPM suitable for use is one or more of four possible isomers of dipropylene glycol methyl ether. The most common isomer is the secondary alcohol resulting from the reaction of PM-1 with propylene oxide (1-methoxy-2-propanol, 2-hydroxypropyl ether), but any combination of isomers can be used. DPM is commercially available from Lyondell Chemical Company as ARCOSOLV® DPM.

When DPM is the starter for the alkoxylation reaction, it is reacted with from 0.5 to 1.5 equivalents of propylene oxide. Preferably, propylene oxide is used in an amount within the range of 0.8 to 1.2 equivalents. lo Most preferred is the range from 0.9 to 1.1 equivalents.

Suitable alkoxylation catalysts have already been described.

The reaction of DPM and PO produces an alkoxylation mixture comprising unreacted DPM, TPM, and higher PM propoxylates. This reaction mixture often contains too much DPM to be valuable for froth flotation. Consequently, the alkoxylation mixture is normally distilled by any suitable technique, including vacuum stripping, to remove DPM and provide an alkylene glycol ether composition comprising at least 30 wt. % of TPM and less than 20 wt. % of DPM. As indicated earlier, such a mixture provides acceptable results in a laboratory-scale froth test used to approximate good performance in the field for recovering platinum values by froth flotation. The alkylene glycol ether composition preferably comprises less than 15 wt. % of DPM. Most preferably, the amount of DPM is within the range of 4 to 12 wt. %.

If desired, the alkoxylation catalyst can be removed from the alkylene glycol ether composition. For example, the composition can be neutralized and filtered or it can be treated with an adsorbant such as magnesium silicate to remove the alkoxylation catalyst. When a basic alkoxylation catalyst is used, it is normally removed. Ideally, however, the catalyst is not removed and the alkylene glycol ether composition is simply used "as is" in the frother application.

The invention provides an effective yet inexpensive product for use in metal recovery from metallic ores. Compared with TPM, the alkoxylated glycol ether compositions of the invention are cheaper and require less purification. On the other hand, the performance attributes of the alkylene glycol ether compositions of the invention should rival or exceed those of TPM or other polyether frother compositions.

The alkylene glycol ether compositions of the invention are useful as frothing agents for recovering metals from metallic ores generated in mining operations, especially platinum or copper. For details of how to use frothing agents to recover metal values by froth flotation, see U.S. Pat. Nos. 2,611,485, 2,695,101, 3,595,390, 4,929,344, and 5,232,581, the teachings of which are incorporated herein by reference.

The following examples merely illustrate the invention. Those skilled in the art will recognize many variations that are within the spirit of the invention and scope of the claims.

EXAMPLE 1

Propoxylation of PM followed by Distillation

A reactor is charged with propylene glycol methyl ether ("PM," 2616 g, 29 mol). Potassium hydroxide flakes (9 g) are stirred into the PM, and the mixture is heated to about 115° C. Propylene oxide (a total of 3.38 kg, 58 mol) is added slowly at first to the stirred mixture until an exotherm indicates commencement of propoxylation. The PO addition rate is then increased slowly to the maximum desirable rate. The reaction temperature is regulated within the range of 110° C. to 120° C., and the addition is complete within about 3 h. Following PO addition, the reaction mixture is held at about 115° C. for about 3 h to consume residual PO.

Residual volatiles, including PM and some dipropylene glycol methyl ether (DPM), are removed by vacuum stripping the mixture at 115° C., 25-50 mm Hg. Stripping continues until the DPM concentration in the pot is reduced to 4.8 wt. % and the tripropylene glycol methyl ethers (TPM) concentration increases to 48 wt. %. The reactor contents are cooled (50-60° C.) and neutralized (to pH=7) with glacial acetic acid.

EXAMPLE 2

Propoxylation of DPM Followed by Distillation

A reactor is charged with dipropylene glycol methyl ether ("DPM," 3585 g, 24 mol). Potassium hydroxide flakes (15 g) are stirred into the DPM, and the mixture is heated to about 140° C. Propylene oxide (a total of 1.4 kg, 58 mol) is added slowly at first to the stirred mixture until an exotherm indicates commencement of propoxylation. The PO addition rate is then increased slowly to the maximum desirable rate. The reaction temperature is maintained at about 140° C., and the addition is complete within 1 h. Following PO addition, the reaction mixture is held at about 140° C. for 3 h to consume residual PO.

Residual volatiles, including DPM, are removed by vacuum stripping the mixture at 140° C., 25-50 mm Hg. Stripping continues until the DPM concentration in the pot is reduced to 12 wt. % and the TPM concentration increases to 42 wt. %. The reactor contents are cooled (50-60° C.) and neutralized (to pH=7) with glacial acetic acid.

COMPARATIVE EXAMPLE 3

Propoxylation of PM—No Distillation

The procedure of Example 1 is generally followed, except that the vacuum stripping step is omitted. The DPM concentration in the pot is 30 wt. %; TPM: 40 wt. %.

COMPARATIVE EXAMPLE 4

Ethoxylation of PM

The procedure of Example 1 is generally followed, except that 2250 g of PM is used, and ethylene oxide (3.75 kg) is used instead of propylene oxide. Vacuum stripping is used to reduce the level of DPM equivalents (i.e., monoethoxylated PM) to 4.6 wt. %; TPM equivalents (diethoxylated PM): 12 wt. %.

COMPARATIVE EXAMPLE 5

Ethoxylation of PM

The procedure of Example 1 is generally followed, except that 2637 g of PM is used, and ethylene oxide (3.36 kg) is used instead of propylene oxide. Vacuum stripping is used to reduce the level of DPM equivalents (i.e., monoethoxylated PM) to 7.6 wt. %; TPM equivalents: 18 wt. %.

COMPARATIVE EXAMPLE 6

Ethoxylation of DPM

The procedure of Example 2 is generally followed, except that 4803 g of DPM is used, and ethylene oxide (1.20 kg) is used instead of propylene oxide. Vacuum stripping is used to reduce the level of DPM to 6.1 wt. %; TPM equivalents (monoethoxylated DPM): 25 wt. %.

Frother Test Results

Each of the frother compositions prepared in Examples 1-2 and Comparative Examples 3-6 is used in a simple laboratory test to approximate its suitability for use in froth flotation. In the test, a small proportion (<1 wt. %) of frothing agent is combined and agitated vigorously with an aqueous sample containing particles of platinum-containing ore. The height of the froth (in mm) and its collapse rate (in mm/s) are determined as a function of frother concentration (in ppm). A pass rating indicates that the frother is likely to be useful in the field for platinum recovery in the mining industry. Results appear in Table 1.

TABLE 1

Frother Test Results

| | \multicolumn{6}{c}{Example} | | | | | |
|---|---|---|---|---|---|---|
| | 1 | 2 | C3 | C4 | C5 | C6 |
| Epoxide | PO | PO | PO | EO | EO | EO |
| Starter | PM | DPM | PM | PM | PM | DPM |
| Epoxide/starter (m/m) | 2.0 | 1.0 | 2.0 | 3.4 | 2.6 | 0.8 |
| DPM (or equiv.[1]), wt. % | 4.8 | 12 | 30 | 4.6 | 7.6 | 6.1 |
| TPM, wt. % | 48 | 42 | 40 | 12 | 18 | 25 |
| Frother test result | pass | pass | fail | fail | fail | fail |

[1] When EO is used, monoethoxylated PM is the DPM equivalent.
EO = ethylene oxide, PO = propylene oxide, PM = propylene glycol methyl ether, DPM = dipropylene glycol methyl ethers; TPM = tripropylene glyol methyl ethers As the results demonstrate, the ethoxylated alkylene glycol ethers did not provide stable froths regardless of the level of DPM equivalents present (Comparative Examples 4-6). The propoxylated PM of Comparative Example 3, prepared by reacting 2 equivalents of PO with PM and containing 30 wt. % of DPM, also failed the froth test. We surprisingly found that a subsequent distillation to reduce the DPM level to less than 20 wt. %, preferably less than 15 wt. %, allowed the alkylene glycol ether composition to pass the froth test with either PM or DPM as the starter and PO as the epoxide (Examples 1 and 2).

The preceding examples are meant only as illustrations. The following claims define the invention.

I claim:

1. A process which comprises:
   (a) reacting propylene glycol methyl ether (PM) with from 1.5 to 3 equivalents of propylene oxide in the presence of an alkoxylation catalyst to produce an alkoxylation mixture comprising PM, dipropylene glycol methyl ethers (DPM), tripropylene glycol methyl ethers (TPM), and higher PM propoxylates; and
   (b) distilling PM and DPM from the alkoxylation mixture to provide an alkylene glycol ether composition comprising at least 30 wt. % of TPM and from 4 to 12 wt. % of DPM.

2. A glycol ether composition made by the process of claim 1.

3. A froth flotation method which comprises recovering a metal from a metallic ore in the presence of a frothing agent comprising the composition of claim 2.

4. The method of claim 3 wherein the metal is selected from the group consisting of platinum and copper.

5. A process which comprises:
   (a) reacting DPM with from 0.5 to 1.5 equivalents of propylene oxide in the presence of an alkoxylation catalyst to produce an alkoxylation mixture comprising DPM, TPM, and higher DPM propoxylates; and
   (b) distilling DPM from the alkoxylation mixture to provide an alkylene glycol ether composition comprising at least 30 wt. % of TPM and from 4 to 12 wt. % of DPM.

6. An alkylene glycol ether composition made by the process of claim 5.

7. A froth flotation method which comprises recovering a metal from a metallic ore in the presence of a frothing agent comprising the composition of claim 6.

8. The method of claim 7 wherein the metal is selected from the group consisting of platinum and copper.

* * * * *